United States Patent [19]

Lewis et al.

[11] Patent Number: 4,525,146
[45] Date of Patent: Jun. 25, 1985

[54] NATURAL APPEARING POSTERIOR TEETH FOR DENTURE PLATES AND THE LIKE

[76] Inventors: Arnold Lewis, R.D. 4, Cadiz, Ohio 43907; Norman R. Hagen, 1463 Shirley Ave., Tacoma, Wash. 98406

[21] Appl. No.: 562,478

[22] Filed: Dec. 19, 1983

[51] Int. Cl.³ .............................................. A61C 13/08
[52] U.S. Cl. .................................................. 433/198
[58] Field of Search .................... 433/197, 198, 202

[56] References Cited

U.S. PATENT DOCUMENTS

Re. 20,234  1/1937  Berry ..................................... 433/197
3,583,070  10/1969  Nietert et al. ........................ 433/198

FOREIGN PATENT DOCUMENTS 634766  3/1950  United Kingdom ................ 433/198

*Primary Examiner*—Robert Peshock
*Attorney, Agent, or Firm*—Shlesinger, Arkwright, Garvey & Fado

[57] ABSTRACT

Natural appearing posterior teeth for denture plates and the like, comprising a plurality of generally longitudinally aligned inner connected synthetic teeth, including at least a first and second molar and a bicuspid; each of the teeth including a crown; a cutting bar having substantial height secured in the teeth and including a portion extending a relatively short distance above the crown of each of the teeth for providing a masticating surface; the cutting bar is continuous and of a generally sinusoidal configuration and includes a plurality of crests; a first crest is disposed in first molar; a plurality of crests are disposed in the second molar; and, at least a crest portion is disposed in the bicuspid.

12 Claims, 6 Drawing Figures

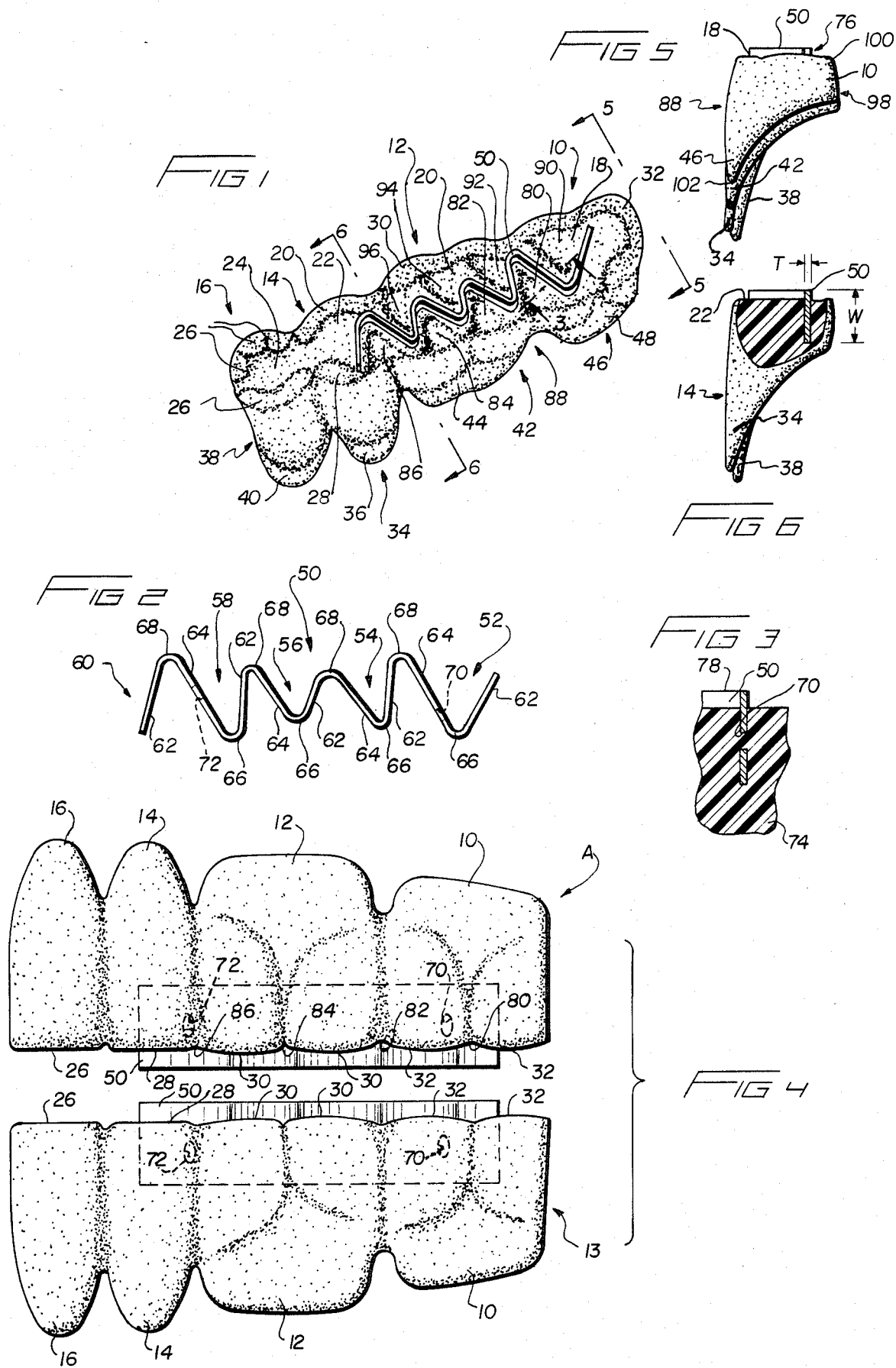

NATURAL APPEARING POSTERIOR TEETH FOR DENTURE PLATES AND THE LIKE

BACKGROUND OF THE INVENTION

The use of porcelain or synthetic artificial teeth in combination with denture plates and dental bridges is well known in the art. The artificial teeth permit the wearer to enjoy the benefits of teeth after the wearer's natural teeth have been removed. When the artificial teeth are used in combination with a denture plate then the teeth are secured to the plate and the plate is disposed over the gums of the wearer. There is a naturally occurring tendency for the gums of the wearer to shrink as the wearer ages with the result that mastication or chewing becomes increasingly difficult as the wearer is unable to apply sufficient pressure to the teeth to perform the mastication process. Additionally, the shrinkage of the gums causes the wearer to experience pain or discomfort because of the improper fitting of the plate with the gums.

An artificial tooth includes a tooth body and an upper crown surface. The crown includes a plurality of cusps extending from the crown and interdigitating with the cusps of an oppositely disposed aligned tooth. The interdigitation, of an upper tooth with a lower tooth, permits the mastication process to occur because of the grinding action occasioned by the movement of the cusps relative to each other when a food product is disposed between the teeth. The prior art artificial teeth required a complicated alignment process, with an equally complicated alignment apparatus, in order that the cusps of one tooth be properly interdigitated with the cusps of the oppositely aligned tooth. Should the cusps not be properly aligned, then the teeth will not function properly. Consequently, the prior art artificial teeth greatly increase the expense to the wearer due to the need for aligning the cusps.

Prange, U.S. Pat. No. 2,295,864, discloses an artificial tooth in which metal cusps are provided at generally the periphery of the crown in order to eliminate the need for aligning the cusps of the prior art artificial teeth, both synthetic and porcelain. The metal cusps of Prange while not requiring alignment of the cusps do increase the cost of artificial teeth as one metal cusp is provided for each artificial tooth. Additionally, the artificial teeth of Prange are individually molded and manufactured and each of the teeth must be individually secured to the plate. Furthermore, the metal cusps of Prange are difficult to manufacture and the securement of the metal cusps in the synthetic artificial teeth is a complicated procedure with the result of increased costs.

Howmedica, Inc., of 5101 South Keeler Avenue, Chicago, Ill., 60632, manufactures artificial teeth under the trade name Micromold Plastic Teeth and claims the benefit of the Prange patent. The artificial teeth of Howmedica are not, however, naturally appearing as the teeth depart quite dramatically from the visual effect of natural teeth. The Howmedica teeth includes three teeth which are interconnected and in which a zigzag cutter bar is disposed where the cusps of Prange were positioned. The Howmedica teeth do not have the natural look of real teeth because the zigzag of the cutter bar is disposed between the inner and outer side surfaces of the teeth with the effect that the teeth must conform to the shape of the cutter bar rather than the cutter bar conforming to the shape of the teeth. Additionally, the Howmedica cutter bar is secured in the teeth by the hardening of the synthetic resin and no means are provided for securely seating the cutter bar otherwise. Furthermore, the teeth of Howmedica are not naturally appearing as they lack the undercut associated with real teeth and this lack of undercut is due to the method of manufacture.

The present invention discloses and claims a unique cutter bar configuration which is adapted to permit the artificial synthetic teeth to be naturally appearing, including the undercuts associated with real teeth, while still permitting the mastication process without the need for interdigitating the cusps. The cutter bar of the present invention provides a series of crests which are disposed along the crown of a plurality of interconnected artificial synthetic teeth in a unique configuration which facilitates the mastication process when upper and lower teeth are employed. The manufacture of the teeth of the present invention is much simpler and less complicated than prior art artificial teeth manufacturing processes with the result that the cost of the teeth may be kept to a minimum. The cutter bar of the present invention also includes means for securely positioning the cutter bar means in the artificial teeth with the result that greater amounts of pressure may be applied to the cutter bar. Consequently, the disclosed invention provides a novel cutting bar means in combination with a plurality of interconnected longitudinally aligned artificial teeth which greatly facilitates the use of artificial teeth while reducing the cost to the ultimate consumer.

OBJECTS AND SUMMARY OF THE INVENTION

A primary object of the disclosed invention is to provide natural appearing artificial posterior teeth overcoming the above noted disadvantages while simultaneously reducing the cost of the teeth to the consumer.

An additional object of the disclosed invention is to provide naturally appearing artificial posterior teeth which are longitudinally aligned and adapted to be positively secured to a denture plate.

Another object of the disclosed invention is to provide each of the natural appearing artificial posterior teeth with a masticating surface in order to permit the wearer to masticate without pain or discomfort.

Yet still an additional object of the disclosed invention is to provide naturally appearing artificial posterior teeth having an improved cutter bar secured in the teeth and which acts as a mastication surface.

Yet a further object of the disclosed invention is to provide naturally appearing artificial posterior teeth which include cutter bar means having means for positively securing the cutter bar means to the teeth.

Yet another object of the disclosed invention is to provide natural appearing posterior teeth which may be mounted to either the upper or the lower denture plate with the result that the cutting bar of one set of teeth is oppositely disposed relative to the cutting bar of the other set of teeth.

Still yet an additional object of the disclosed invention is to provide a uniquely configured cutting bar which permits the artificial teeth to be natural appearing while still providing maximum mastication surface area.

Yet a further object of the disclosed invention is to provide sluice-ways between the crests of the cutting bar in order to flush out masticated food products.

Yet still another object of the disclosed invention is to provide a removable tooth secured to the teeth having the cutting bar in order to permit the set of teeth to be sized to fit any denture.

Still yet an additional object of the disclosed invention is to provide natural appearing artificial teeth which are anatomically correct in appearance.

Yet still a further object of the disclosed invention is to provide a process for manufacture of the teeth which is simpler and less costly than prior art manufacturing processes.

These and other objects and advantages of the invention will be readily apparent in view of the following description and drawings of the above-described invention.

DESCRIPTION OF THE DRAWINGS

The above and other objects and advantages and novel features of the present invention will become apparent from the following detailed description of the preferred embodiment of the invention illustrated in the accompanying drawings, wherein:

FIG. 1 is a perspective view of the teeth and cutter bar of the invention;

FIG. 2 is a top plan view of the cutter bar of FIG. 1 with portions shown in phantom;

FIG. 3 is a fragmentary cross-sectional view taken along the section 3—3 of FIG. 1 and disclosing the aperture used for securing the cutter bar in the teeth;

FIG. 4 is a side-elevational view of an upper and lower set of teeth with portions of the cutter bars shown in phantom;

FIG. 5 is a rear-elevational view taken along the line 5—5 of FIG. 1; and,

FIG. 6 is a cross-sectional view taken along the section 6—6 of FIG. 1.

FIG. 7 is a plan view of the cutter bars of the teeth of FIG. 4 with portions of the teeth broken away.

DESCRIPTION OF THE INVENTION

As best shown in FIG. 1, a first or twelve year molar 10 is connected to and aligned with a second molar 12. Second molar 12 is connected to and aligned with a first bicuspid 14 which is similarly aligned and connected with a second bicuspid 16. The teeth 10, 12, 14 and 16 are, preferably, manufactured from polymethyl methacrylate. Polymethyl methacrylate is a colorless resin which hardens into a ceramic-like mass which is suitable for the production of teeth. Preferably, the polymethyl methacrylate resin is colored so as to be as close as possible to the color of the original teeth of the wearer, as well as to be anatomically accurate. Polymethyl methacrylate provides a hardened exterior surface which is not susceptible to wear or attack by saliva of the wearer and, therefore, provides a suitable composition for the manufacture of teeth.

Each of the teeth 10, 12, 14 and 16 has an upper crown, 18, 20, 22 and 24, respectively. The crown 24 of second bicuspid 16 includes a number of ridges or cusps 26 which are arrayed along the periphery of bicuspid 16 in order to provide a masticating surface in combination with the crown 24 as will be explained herein later. Similarly, first bicuspid 14 includes a number of similar ridges or cusps 28 to perform the similar purpose. The crown 20 of second molar 12 includes a number of ridges or cusps 30 along the periphery thereof in order to improve the natural appearance of the second molar 12 so that it will be anatomically correct. Similarly, first molar 10 includes ridges or cusps 32 so that it will also be anatomically correct and natural appearing.

First bicuspid 14 includes a root portion 34, including an undercut 36 in order that the bicuspid 14 will be anatomically accurate. Additionally, second bicuspid 16 includes a root portion 38 with an undercut 40 so that it will be anatomically correct. As best shown in FIG. 5, root portion 38 of second bicuspid 16 extends downwardly a distance greater than does root portion 34 of first bicuspid 14.

As best shown in FIG. 1, second molar 12 includes a root portion 42 with an undercut 44 and the root portion 34 of first bicuspid 14 extends downwardly a distance greater than does the root portion 42 of second molar 12, as best shown in FIG. 5. Similarly, first molar 10 has a root portion 46 and an undercut 48 and root portion 42 of second molar 12 extends downwardly a distance greater than does the root portion 46 or first molar 10. In this way, the combination of the root portions 34, 38, 42 and 46 and the undercuts 36, 40, 44 and 48 combine to provide naturally appearing artificial teeth which are anatomically correct. The natural appearance of the teeth 10, 12, 14 and 16 is very important to the wearer because frequently the wearer of artificial teeth will be embarrassed or otherwise discomforted by the thought that the teeth are not natural appearing.

Sinusoidal cutter bar 50 is securely mounted in first molar 10, second molar 12 and first bicuspid 14. Cutter bar 50 is preferably manufactured from a type 302 or 304 stainless steel. As best shown in FIG. 6, cutter bar 50 has a height W of approximately 0.15 inches and a thickness T of approximately 0.025 inches. In this way, cutter bar 50 has substantial thickness and substantial height in order to facilitate mastication.

As best shown in FIG. 2, cutter bar 50 includes a plurality of crests 52, 54, 56 and 58 and a crest portion 60. The crests 52, 54, 56 and 58 and crest portion 60 are arranged in a generally sinusoidal configuration and the cutter bar 50 is continuous. Each crest, 52, 54, 56 and 58 includes two angularly disposed generally straight linear sections 62 and 64 with a convex rounded portion 66 connecting linear sections 62 and 64 and spanning its respective crown longitudinally and laterally a significant distance. A concave portion 68 connects the linear sections 64 of one crest, such as crest 52, to the linear section 62 of an adjacent crest, such as crest 54. In this way, the continuity of cutting bar 50 is maintained.

It will be noted in FIG. 2 that the concave portion 68 connecting linear section 64 of crest 52 to linear section 62 of crest 54 is longitudinally aligned with the concave portion 68 connecting linear section 64 of crest 58 to linear section 62 of crest portion 60. Similarly, convex portion 66 of crest 52 is longitudinally aligned with the convex portion 66 of crest 58. Convex portion 66 of crest 54 extends outwardly a distance greater than does convex portion 66 of crest 56. Similarly, concave portion 68 connecting linear section 64 of crest 54 to linear section 62 of crest 56 does not extend outwardly as far as does the concave portion 68 connecting linear section 64 of crest 52 to linear section 62 of crest 54. The outward and inward extension of the crests 52, 54, 56 and 58 serves to enhance the natural appearance and the anatomical correctness of the teeth 10, 12 and 14, while permitting maximum chewing pressure to be applied.

Crest 52 spans crown 18 laterally and longitudinally a significant distance. Crests 54, 56 and 58 each span crown 20 a distance less than does crest 52. Finally, portion 60 spans laterally and longitudinally along crown 22 a substantial distance. The distances that the crests 52, 54 and 56 span longitudinally and laterally along crowns 18, 20 and 22 permits maximum surface area for mastication as well as maximum application of chewing pressure without destroying the anatomical appearance of the teeth 10, 12 and 14.

As best shown in FIGS. 2 and 3, cutting bar 50 includes an aperture 70 disposed in linear portion 64 of crest 52. A similar aperture 72 is disposed in linear section 64 of crest 58. As best shown in FIG. 3, the polymethyl methacrylate resin from which the tooth 10, as well as the teeth 12, 14 and 16 are manufactured, fills the aperture 70 and in this way positively secures and anchors the cutting bar 50 rigidly because the polymethyl methacrylate resin 74 hardens in the aperture 70 and in this way prevents any movement of the cutting bar 50 in the solidified resin. As should be obvious to one skilled in the art, a similar filling of the aperture 72 is accomplished when the polymethyl methacrylate resin hardens during the formation of bicuspid 14. It should be noted in FIG. 2, that the apertures 70 and 72 are not coaxial and are not disposed upon the longitudinal center line of cutting bar 50 and in this way the compressive forces associated with mastication are spread out and therefore minimize the possibility of the breakage of the resin 74 filling the apertures 70 and 72.

As best shown in FIG. 4, cutting bar 50 extends beyond ridges or cusps 32, 30, 28 and 26, respectively. As best shown in FIG. 5, cutting bar 50 extends a relatively short distance beyond crown 18. Preferably that portion 76 of cutting bar 50 extending beyond crown 18 extends 0.015 inches after the cutting bar 50 has been polished and machined so that the cutting bar 50 will be at a constant elevation or level plane when the teeth 10, 12, 14 and 16 are secured to a denture plate (not shown). In this way, the cutting bar 50 does not have any ridges or undulations which would prevent proper mastication. It can be appreciated that the upper surface 78 of cutting bar 50, because of its polished finish as well as its significant thickness, provides a masticating surface.

As best shown in FIG. 4, a set of teeth A and a set of teeth B which are each identical to the teeth 10, 12, 14 and 16, are shown disposed as they would be when attached to denture plates (not shown). One skilled in the art will appreciate that the sinusoidal configuration of the cutting bar 50 disposed within set A will be rotated 180° relative to the sinusoidal configuration of the cutting bar 50 disposed in set B. This is dissimilar to prior art cutting bars in which the cutting bars are each aligned so that they overlap. The prior art required, therefore, two different sets of teeth to be manufactured, as opposed to the present invention. Additionally, because the cutting bar 50 of the sets A and B are not configuratively aligned, the mastication process is facilitated because the grinding action is increased and maximum pressure is applied at the point where the cutting bar 50 of set A meets the cutting bar 50 of set B. This maximization of the pressure point greatly facilitates mastication.

As best shown in FIGS. 1 and 4, each of the teeth 10, 12, 14 and 16 includes sluice-ways disposed between vertical sections 62 and 64 of an associated crest. Sluiceways 80, 82, 84 and 86 extend from an associated concave portion 68 outwardly and downwardly toward outer side portion 88 of interconnected teeth 10, 12, 14 and 16. Similarly, sluice-ways 90, 92, 94 and 96 extend from an associated convex portion 66 to inner side portion 98 of interconnected teeth 10, 12, 14 and 16. The sluice-ways 80, 82, 84 and 86 and 90, 92, 94 and 96 serve to permit masticated food products to be flushed out from between the crest 52, 54, 56 and 58 and from between the interlocked linear section 62 and 64. This prevents the build-up of food products above the surface 78 of cutting bars 50 which would therefore inhibit efficient mastication by cutting bars 50. The sluice-ways 80, 82, 84 and 86 and 90, 92, 94 and 96, slope generally in a valley-type manner from adjacent the cutting bar means 50 to the inner side portion 98 or the outer side/portion 88, as appropriate. Consequently, the natural flow of the saliva causes any masticated food product to be flushed out.

FIG. 7 discloses the cutting bars 50 of the sets of teeth A and B in their cooperating relationship when the sets of teeth A and B are brought together for chewing. It can be seen that the cutting bars 50 of the sets A and B cooperate such that the crests 52-60 of the cutting bar 50 of set A are oriented and extend in a direction opposite to the direction and orientation in which the crests 52-60 of the cutting bar 50 of set B extend. The cooperating cutting bars 50 provide longitudinally aligned mastication openings 100, 102, 104, 106, 108, 110, 112, and 114 when the masticating surfaces 78 of the cutting bars 50 are brought substantially into engagement for chewing purposes. It can be noted that the mastication openings 100 and 114 which are provided by the first crest 52 and the last crest 60, respectively, have an opening area substantially exceeding the area defined by the crests 54-58. Chewing action imparted to the sets A and B by the jaws of the wearer (not shown) causes the mastication openings 100-114 to open and close and to thereby permit the chewing of food products disposed between the sets A and B.

The manufacture of the interconnected teeth 10, 12, 14 and 16 proceeds in a method dissimilar to that of the prior art. The first step is to provide a mold which has the configuration of the teeth as well as a slot for accepting the cutting bars 50. Preferably, the slot is approximately 0.025 inches deep and has the configuration of the cutting bar 50 and serves to hold the cutting bar during the molding of the teeth 10, 12, 14 and 16. The slot for holding the cutting bar 50 is disposed in the bottom of the mold and, consequently, the teeth 10, 12, 14 and 16 have their crowns 18, 20, 22 and 24, respectively, disposed horizontally.

The mold for manufacturing the teeth 10, 12, 14 and 16 is, preferably, manufactured from a berryllium copper alloy the interior of which has been chrome plated to prevent damage to the mold during the extraction of the molded teeth 10, 12, 14 and 16. One skilled in the art will appreciate that any mold sufficient to permit the compression molding of polymethyl methacrylate requires two cooperating members with the result that a mold line is normally evident after the operation is completed. Preferably the molds are disposed so that the mold line extends angularly from the point 100 to the point 102, as best shown in FIG. 5, with the result that the mold line is hidden from view when the teeth are mounted to a denture plate (not shown). In this way, the mold line extends from the inner side portion 98 in the area of the relevant crown 18, 20, 22 and 24 to the tip of the root portion 34, 38, 42 and 46, respectively.

The fact that the teeth 10, 12, 14 and 16 are manufactured with their crown 18, 20, 22 and 24, respectively, face down permits a plurality of teeth to be manufactured from a given set of molds and the ease of manufacturing is facilitated because no external means are necessary for positioning the cutting bars 50 in the mold. The prior art teeth were manufactured with their crowns vertically disposed with the effect that means had to be provided for maintaining the cutting bars so that they would not be displaced from the mold.

After the mold has been prepared, then a biscuit, that is a pre-determined amount of polymethyl methacrylate, is positioned within the mold and is colored to give the teeth 10, 12, 14 and 16 their eventual color. The dies of the mold set are then closed and the polymethyl methacrylate biscuit is compression molded into the configuration of the teeth 10, 12, 14 and 16. The compression molding is important in order to prevent acid breakdown, from acid contained in the saliva, from attacking the finished teeth 10, 12, 14 and 16.

From the above, it can be seen that a generally two-step manufacturing process has been outlined. The prior art had required the additional step of providing a clear portion basically configured similar to the outer side portion of the teeth. This outer side portion was then colored and then the cutting bar was placed in position and the biscuit was molded. Consequently, the present manufacturing process is more efficient than the prior art processes with the result that costs of manufacturing are decreased.

While this invention has been described as having a preferred design, it is understood that it is capable of further modifications, uses and/or adaptations of the invention following in general the principles of the invention including such departures from the present disclosure as come within known or customary practice in the art to which the invention pertains and as may be applied to the central features hereinbefore set forth, and fall within the scope of the invention of the limits of the appended claims.

What we claim is:

1. Natural appearing posterior teeth for denture plates and the like comprising:
   (a) a plurality of generally longitudinally aligned interconnected synthetic teeth, including at least a first and a second molar and a bicuspid;
   (b) each of said teeth including a crown;
   (c) cutting bar means having substantial height secured in said at least a first and second molar and a bicuspid and including a portion extending a relatively short distance above the crown of each of said at least a first and second molar and a bicuspid for providing a masticating surface;
   (d) said cutting bar means being continuous and of a generally sinusoidal configuration and including a plurality of crests;
   (e) a first crest disposed in said first molar and standing generally longitudinally and laterally a substantial distance along said first molar crown;
   (f) a plurality of crests disposed in said second molar, each of said plurality of crests extending generally longitudinally and laterally along said second molar crown a distance less than said first distance;
   (g) a last crest disposed in said bicuspid and extending generally longitudinally and laterally a substantial distance along said bicuspid crown and wherein said plurality of crests include at least two crests extending in the same direction and having a trough to peak spacing less than the trough to peak spacing of said first and last crests.

2. The teeth of claim 1, wherein:
   (a) said cutting bar means including at least a first aperture therethrough associated with one of said teeth; and,
   (b) said teeth comprised of a hardened synthetic material and said material filling said at least a first aperture for securing said cutting bar means in said teeth.

3. The teeth as defined in claim 2, wherein:
   (a) said cutting bar means including a first and second aperture; and,
   (b) said first aperture associated with said first crest and said second aperture disposed adjacent said last crest.

4. The teeth as defined in claim 3 wherein:
   (a) said first and second apertures being non-coaxial.

5. The teeth as defined in claim 1, wherein:
   (a) each of said crest including two angularly disposed generally linear sections integral with and connected to a generally convex curved portion; and,
   (b) at least one of said linear sections connected to a linear section of an adjacent crest by a generally concave curved portion.

6. The teeth as defined in claim 1, wherein:
   (a) said second molar including a first, a second, and a third crest;
   (b) said first crest of said second molar having a first linear section connected to a first linear section of said second crest of said second molar; and,
   (c) said first linear sections being of substantially equal length.

7. The teeth as defined in claim 6, wherein:
   (a) said convex portions of said first and third crests of said second molar disposed nearer said outer side portion than said convex portion of said second crest of said second molar.

8. The teeth as defined in claim 6, wherein:
   (a) said first molar first crest convex portion and said second molar third crest convex portion being aligned.

9. The teeth as defined in claim 1, further comprising:
   (a) at least another synthetic tooth removably attached to and aligned with said bicuspid.

10. Natural appearing posterior teeth for mounting to denture plates or the like comprising:
    (a) an upper set of generally longitudinally aligned interconnected synthetic teeth including a first and second molar and a bicuspid;
    (b) a lower set of generally longitudinally aligned interconnected synthetic teeth including a first and second molar and a bicuspid;
    (c) each of said teeth having a crown and said molars and said bicuspid of said lower set aligned with said molars and said bicuspid of said upper set;
    (d) cutting bar means secured in each of said teeth of each of said sets extending beyond and outwardly of the associated crown for providing a masticating surface;
    (e) each of said cutting bar means being continuous and having a generally sinusoidal configuration providing a first crest associated with said first molar and at least two crests associated with said second molar and a last crest associated with said bicuspid and each of said crests extending longitudinally and laterally along the associated crown;
    (f) said crests of each of said sets being oriented in the same direction and said two crests of said second molar having a trough to peak spacing less than the trough to peak spacing of said first and last crests;

(g) said cutting bar means of said sets being oppositely oriented so that the crests of said upper set extend in a direction opposite to the direction in which the crests of said lower set extend;

(h) the masticating surface of said cutting bar means of each of said sets adapted for engagement so that said crests of said upper and lower sets cooperate and define a plurality of mastication openings and said first and last crests providing mastication openings substantially exceeding the area of the mastication openings provided by the two crests of said second molars whereby the chewing action of the jaws causes said mastication openings to open and close and to thereby permit the chewing of food products disposed between said sets.

11. The teeth as defined in claim 10, wherein:

(a) each of said crowns includes sluice ways cooperating with the associated crests for flushing food particles.

12. The teeth as defined in claim 10, wherein:

(a) each of said cutting bar means includes a pair of spaced apart non-coaxial apertures therethrough; and, (b) each of said teeth comprised of a hardened synthetic material and said material filling said apertures for thereby securing said cutting bar means in said teeth.

* * * * *

UNITED STATES PATENT AND TRADEMARK OFFICE
CERTIFICATE OF CORRECTION

PATENT NO. : 4,525,146
DATED : June 25, 1985
INVENTOR(S) : Arnold Lewis et al.

It is certified that error appears in the above-identified patent and that said Letters Patent is hereby corrected as shown below:

Insert Figure 7 as part of Letters Patent.

On the title page "6 Drawing Figures" should read

-- 7 Drawing Figures --.

Signed and Sealed this

Twenty-sixth Day of November 1985

[SEAL]

Attest:

Attesting Officer

DONALD J. QUIGG

*Commissioner of Patents and Trademarks*

UNITED STATES PATENT AND TRADEMARK OFFICE
CERTIFICATE OF CORRECTION

PATENT NO. : 4,525,146                                  Page 2 of 2
DATED     : June 25, 1985
INVENTOR(S) : Arnold Lewis et al.

It is certified that error appears in the above-identified patent and that said Letters Patent is hereby corrected as shown below:

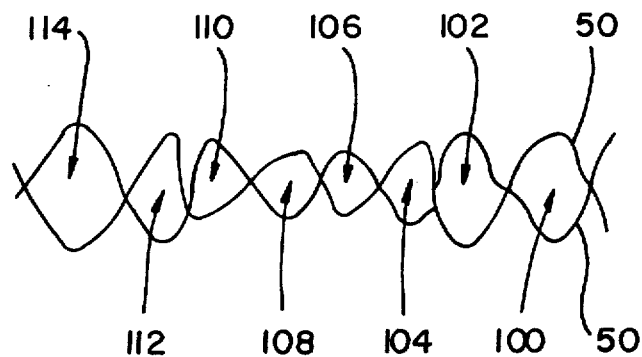

FIG 7